United States Patent [19]

Dietze et al.

[11] Patent Number: 5,282,950
[45] Date of Patent: Feb. 1, 1994

[54] ELECTROCHEMICAL ANALYSIS SYSTEM

[75] Inventors: Werner Dietze, Heidelberg; Hans-Peter Haar, Wiesloch; Wolfgang Obermeier, Heidelberg, all of Fed. Rep. of Germany

[73] Assignee: Boehringer Mannheim GmbH, Mannheim, Fed. Rep. of Germany

[21] Appl. No.: 913,103

[22] Filed: Jul. 14, 1992

[30] Foreign Application Priority Data

Jul. 15, 1991 [DE] Fed. Rep. of Germany ....... 4123348

[51] Int. Cl.$^5$ ............................................. G01N 27/26
[52] U.S. Cl. ..................................... 204/406; 204/407; 204/412; 422/68.1; 422/82.01
[58] Field of Search ............... 204/406, 403, 401, 407, 204/412, 416, 418, 419, 433, 435; 435/817, 291; 422/68.1, 82.01

[56] References Cited

U.S. PATENT DOCUMENTS 4,225,410  9/1980  Pace ..................................... 204/403
4,654,127  3/1987  Baker et al. ......................... 204/409

FOREIGN PATENT DOCUMENTS 0136362   4/1985   European Pat. Off. .
0396788  11/1990   European Pat. Off. .
0417347   3/1991   European Pat. Off. .
2127142  12/1971   Fed. Rep. of Germany .
WO 92/01947  2/1992  World Int. Prop. O. .

OTHER PUBLICATIONS

Sensors and Actuators, vol. 15, No. 4, Dec. 1988, pp. 435-443.

Primary Examiner—John Niebling
Assistant Examiner—Bruce F. Bell
Attorney, Agent, or Firm—Nikaido, Marmelstein, Murray & Oram

[57] ABSTRACT

An electrochemical analysis system for analytical determination of a constituent of a sample includes a disposable analysis element and an evaluation unit. The disposable analysis element includes an isolating carrier with a sample application device for applying a sample thereto for analysis, and at least one sensor with a working electrode and a reference electrode for sensing electrical properties of the sample. The analysis element also includes a connection zone with connecting contacts which are connected to the electrodes via connecting leads. The evaluation unit includes an analysis element connector for electrically connecting to the connecting contacts of the analysis element, and a measuring and evaluation circuit for measuring electrical variation characteristics of the electrical properties sensed by the sensor on the analysis element. This circuit also converts a measured value into an analytical value, and includes a changeover device for changing over connection of an electrical power source with a current measuring device or a voltage measuring device to different connecting contacts of the analysis element.

15 Claims, 4 Drawing Sheets

ELECTROCHEMICAL ANALYSIS SYSTEM

BACKGROUND OF THE INVENTION

1. Field of the Invention

The invention relates to an electrochemical analysis system for the analytical determination of a constituent of a sample, in particular for the analysis of body fluids such as blood or urine. The system consists of disposable analysis elements, which are thrown away after use, and an evaluation unit.

2. Description of the Related Art

Analysis by means of disposable analysis elements has acquired great importance above all in the medical field. Compared with the analytical methods using liquid reagents which were exclusively the norm previously, it is distinguished above all by ease of handling. Analyses are thus able to be carried out with great accuracy by relatively untrained laboratory staff, or even by the patient himself. The evaluation units are comparatively inexpensive, and it is therefore possible to carry out the analysis "close to the patient" in the doctor's surgery or at the hospital station.

The analysis elements contain reagents which on contact with the sample lead to a physically detectable change characteristic of the analysis. In the case of the analysis elements most commonly used in practice the reaction of the reagents with the sample leads to a colour change, which is analysed visually or by reflection photometry.

In addition, there have already existed for a long time developments aimed at applying electrochemical analysis methods, in particular analysis by means of enzyme electrodes, to systems with disposable analysis elements. Such analysis elements have on an isolating carrier in a sample application zone at least one sensor with a working electrode and a reference electrode. The electrodes are connected via connecting leads to connecting contacts, which are located in a connection zone of the analysis element. There may be measured from the connecting contacts the variation in an electrical property of the analysis element, said variation being characteristic of the analysis.

An example of such an analysis element is described in U.S. Pat. No. 4,225,410. It has a large number of different sensors on a single isolating carrier, in order to enable several different analyses to be conducted simultaneously on a sample (for example a drop of blood).

Use is made in this connection of various measuring principles known from the field of electrochemical analysis. In particular a distinction is drawn between potentiometric and amperometric sensors. In the case of potentiometric sensors a voltage is obtained by electrochemical means, which may be measured with high resistance at the connecting contacts. In the case of amperometric sensors, for which the present invention is particularly advantageous, a current flowing at a defined voltage forms the electrical property measurable at the connecting contacts.

The evaluation units of such systems have an analysis element connection plug for the electrical connection to the connecting contacts of the analysis elements and a measuring and evaluation circuit. The measuring and evaluation circuit serves to measure the signal to be measured and to convert the measured value into an analytical value. Various methods are known for the conversion, a microprocessor usually being used. The results are usually represented on a display located on the evaluation unit. They may also be passed to a separate central processing unit and be displayed and/or recorded there.

SUMMARY OF THE INVENTION

The aim of the invention is to provide an electrochemical analysis system in which a very high degree of reliability and accuracy of the analysis is achieved at relatively low cost.

The aim is achieved in the case of an electrochemical analysis system of the kind described in the preamble by the fact that the measuring and evaluation circuit comprises a change-over unit by means of which an electric voltage source with a current measuring device and a voltage measuring device are connectable optionally to different connecting contacts of the analysis element.

There are thus made possible—as will be explained in greater detail below—various controls and checks of the system functions, which refer both to the unit and to the analysis element. The increased security and reliability connected with the latter is achieved with very little outlay on technical equipment, because an electric voltage source and devices for measuring current and voltage are in any case usually provided for the evaluation units of electrochemical analysis systems. At the same time it is possible, due to the optional change-over facility, to evaluate with a simple and inexpensive unit also those analysis elements which contain several sensors for different parameters. Even the measurement of sensors of different types (e.g. amperometric and potentiometric sensors) which are integrated on an analysis element is possible.

The current measuring device and the voltage measuring device are preferably equipped also for the determination of complex signal components, in combination with the electrical voltage source. In this way in particular capacitances may be determined, in order to make additional checks possible. An a.c. voltage source (preferably with switch-selectable or variable frequency) may be used for this purpose. A solution is preferred, however, in which a digital-electronic detection of complex signals is made possible by the use of sufficiently rapid components which permit the determination of decay times.

In order in general to make a time-dependent measurement of voltage and current signals possible, there may be connected between the change-over unit and the voltage measuring device or between the change-over unit and the current measuring device according to a further preferred embodiment in each case a sample and hold circuit. The clocking of the times at which measurements are made by the current measuring and voltage measuring devices is preferably mutually synchronized. Synchronization with the operation of the electric voltage source should also be possible.

According to a particularily prefered embodiment at least one of the electrodes of the analysis elements pertaining to the analysis system has an additional connecting lead to an additional connecting contact.

Said additional connecting lead makes various test and checking functions possible. It is therefore given the name of test lead. For example it makes it possible to determine in a very simple manner the time at which an analysis element is inserted into the evaluation unit. In addition it makes improvements in measuring technique possible, which lead to a rise in the measuring accuracy.

An important advantage of the additional test lead may be seen in the fact that the manufacture of the analysis elements s simplified. With known analysis elements a high outlay is required in order to ensure reproducibly low lead resistances of the connecting leads between the electrodes and the connecting contacts. The analysis elements usually consist of a longitudinal, flat layer of insulating plastics material, to which the sensors, the connecting leads and the contacts are applied as thin strips. In order to ensure the required lead quality, high-quality materials are often applied by expensive methods (e.g. by sputtering or silk screen printing). In the case of one commercially available electrochemical analysis element there is for example chosen for the conductive strips a double-layered construction in which a layer of silver-palladium is applied above a graphite layer. The intention of such measures is in particular to avoid hairline cracks, which could distort the analysis considerably, without this being ascertainable with sufficient reliability in the case of the known methods. The outlay in such production engineering terms may be reduced by the invention.

On the other hand the use of the additional test leads makes possible—as will be explained in detail below—on the one hand with simple means an additional check of the analysis element with the evaluation unit and on the other an improved measurement technique, which is less dependent on the lead resistances of the connecting leads.

Known sensors operate in some cases with only two electrodes (working electrode and reference electrode), in some cases with three electrodes (working electrode, reference electrode and auxiliary electrode). Particularly in the case of analysis elements with two electrodes both the working electrode and the reference electrode are preferably provided with an additional test lead. In the case of sensors with three electrodes it is generally sufficient if only the working electrode comprises an additional test lead.

The invention is of particular advantage in conjunction with analysis elements where the carrier is a flat substrate of isolating material on which the connecting leads (preferably also the electrodes and the connecting contacts) are constructed as conductive strips in the form of a thin conductive layer. Such analysis elements are described for example in EP-A No. 136 362 and in DE-A No. 21 27 142. On the basis of the present invention the conductive strips of such analysis elements may be extremely narrow. This leads to a saving on material and permits a compact manner of construction. The conductive strips may in particular also consist of metal layers applied by vacuum deposition, sputtering or a printing technique. They consist particularly preferably of graphite, which may be applied for example by the silk screen printing method.

BRIEF DESCRIPTION OF THE DRAWINGS

The invention will be explained in detail below with reference to an exemplifying embodiment shown diagrammatically in the figures, where.

DESCRIPTION OF THE PREFERRED EMBODIMENTS

Figure 1:
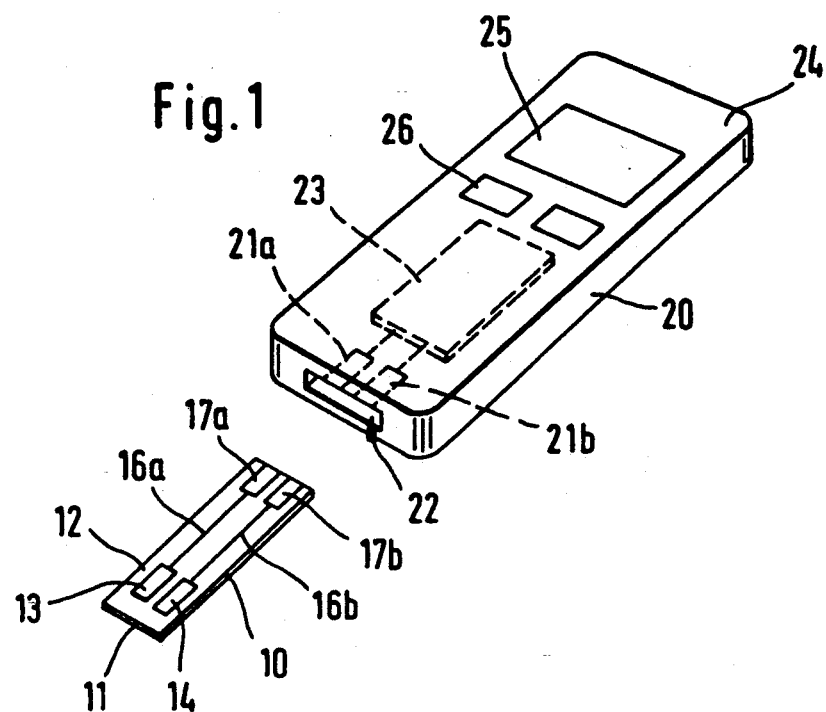
FIG. 1 shows an analysis system according to the invention in perspective.

The analysis system shown in FIG. 1 consists of analysis elements 10 (only one of which is shown) and an evaluation unit 20. On the analysis element 10 there is seen on an isolating substrate 1 of plastics material in a sample application zone 12 a sensor 18. It comprises a working electrode 13 and a reference electrode 14. The electrodes 13, 14 are connected via connecting leads 16a, 16b to a connection zone 19 in which connecting contacts 17a, 17b of the analysis element ("element contacts") are located, by means of which the electrical connection to corresponding contacts 21a, 21b of the evaluation unit 20 ("unit contacts") is made.

The unit contacts 21 are located in an analysis element connection 22. They are connected to a measuring and evaluation circuit 23 in the housing 24 of the evaluation unit 20. The measurement results and any control messages are indicated via a display 25. Keys 26 are provided for the entering of commands and settings.

Figure 2:
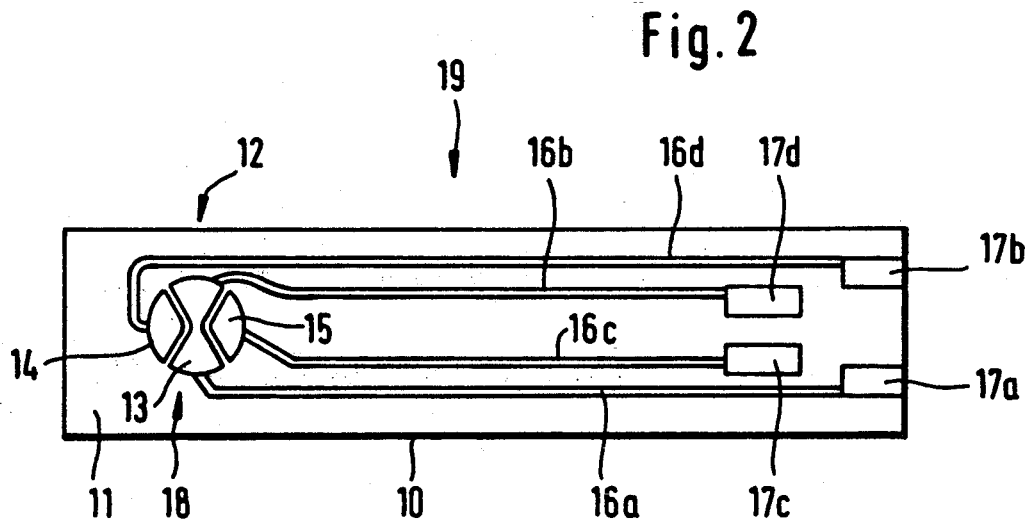
FIG. 2 a top view of a preferred analysis element.

The analysis element 10 shown in FIG. 2 has in its sample application zone 12 a sensor 18 which in addition to a working electrode 13 and a reference electrode 14 comprises an auxiliary electrode 15. The working electrode 13 is arranged between the reference electrode 14 and the auxiliary electrode 15. Material and construction of the electrodes are conventional. The active surface of the working electrode 13 may comprise for example an enzyme and a mediator. The reference electrode 14 and the auxiliary electrode 15 consist preferably of the same material (for example silver/silver chloride) and have active areas of equal size in the sample application zone 12. The electrodes 13, 14 and 15 are connected by a total of four connecting leads 16a to 16d to element contacts 17a to 17d. The latter are with expediency—as shown—offset from one another in the longitudinal direction of the analysis element 10, in order to make an inexpensive narrow method of construction of the analysis element possible with nevertheless sufficient width of the contact surfaces. In the preferred case shown two of the contacts 17a and 17d are connected via separate connecting leads 16a, 16d to the working electrode 13.

Several working electrodes (in particular for the analysis of different constituents of the sample) may also be provided, which are preferably arranged together between a reference electrode and an auxiliary electrode and comprise respectively two separate connecting leads to respectively two element contacts.

Figure 3:
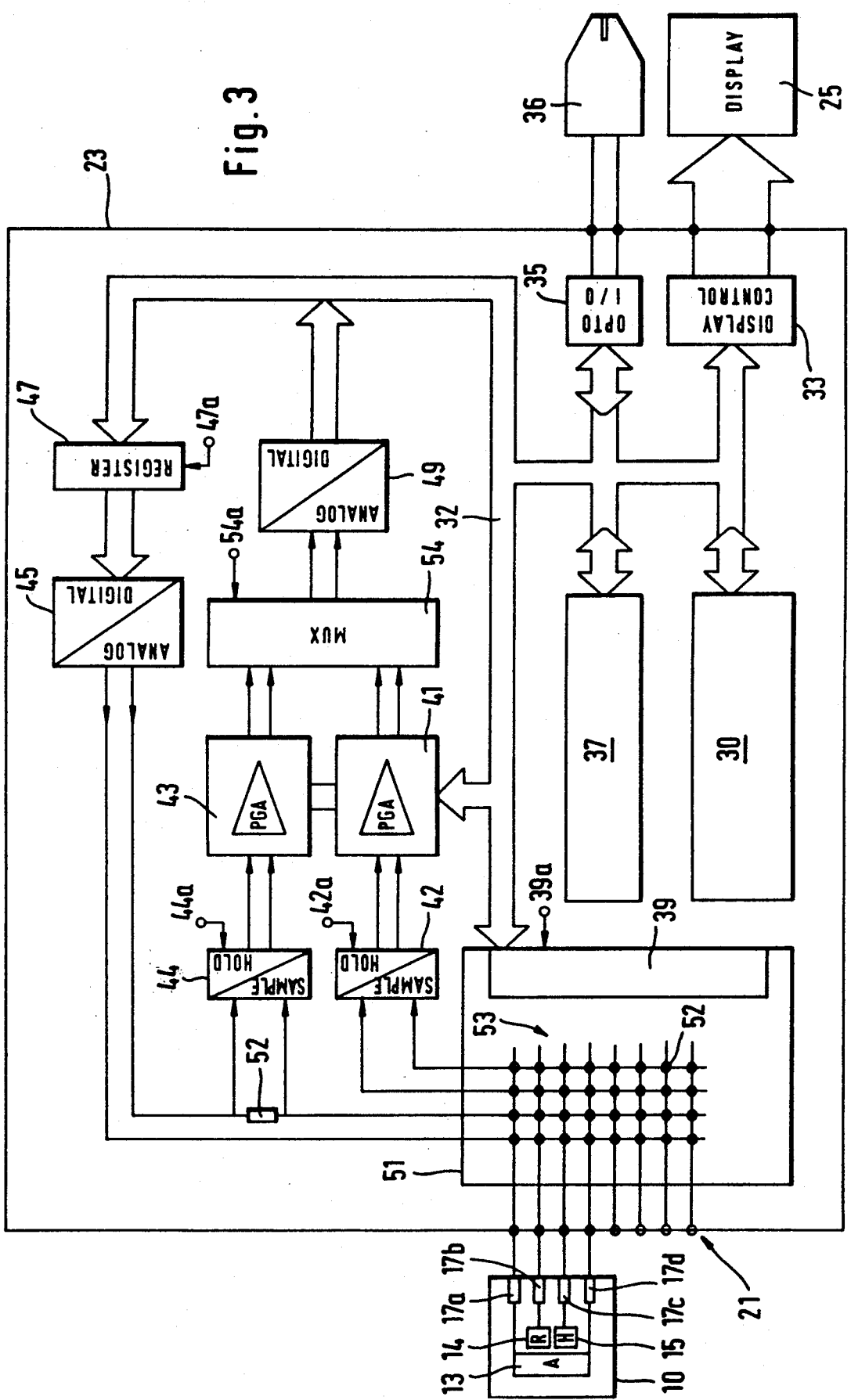
FIG. 3 a block diagram of an analysis system.
Figure 4:
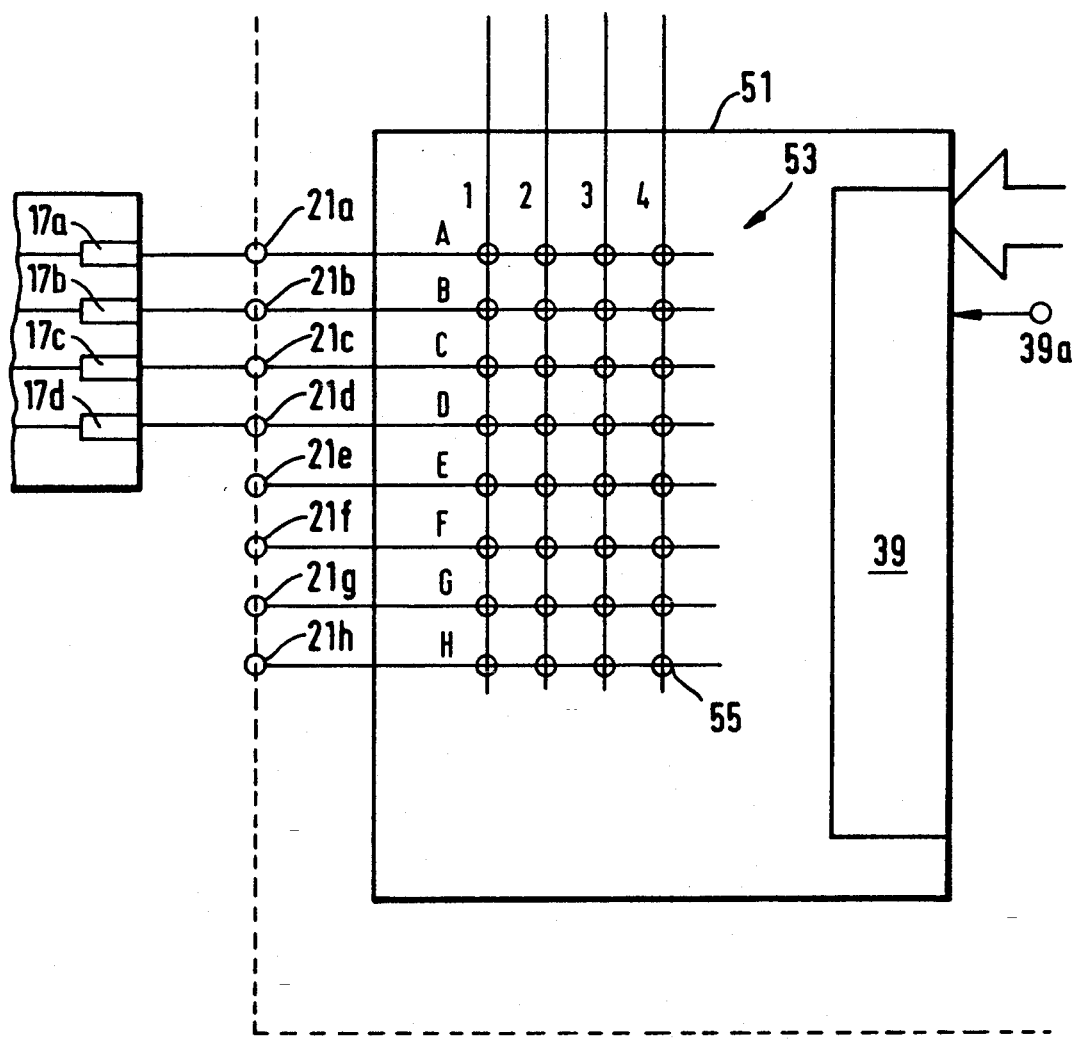
FIG. 4 an enlarged cut-out view from FIG. 3.

In FIGS. 3 and 4 there is seen in highly diagrammatic form an analysis element 10 of the type shown in FIG. 2, which is connected to the measuring and evaluation circuit 23 of a corresponding evaluation unit.

The measuring and evaluation circuit 23 is realized according to digital techniques with a microprocessor. A measurement and control unit 30 serves for user prompting, sequence control and signal processing. It is connected via a data bus 32 to a display control 33, an optoelectronic input/output 35, a calibration value store 37, a switching matrix control logic 39, two amplifiers with programmable gain factor (Programmable Gain Amplifier, PGA) 41 and 43 and (via a register 47) to an electric voltage source 45, whose output voltage can be set digitally. The display control circuit 33 controls the display 25. The opto-electronic input/output 35 may for example serve for the connection of a phototransmitter/receiver unit 36 as a light barrier, optical data interface or bar code reader. The whole of the measuring and evaluation circuit, but at least the switching unit 51, the voltage measuring device 42, 49 and the current measuring device 52, 43, 49, are preferably integrated monolithically as a semiconductor chip.

The PGA amplifier 41 forms together with an analog-to-digital converter 49 a voltage measuring device. The voltage measuring device 41, 49 is connectable by means of a changeover unit 51 optionally and in any polarity to a pair of the unit contacts 21a-21d, to which the analysis element 10 is connected. The voltage source 45 may also be connected via the changeover unit 51 optionally to each pair of the unit contacts 21a-21d and thus to each of the element contacts 17a-17d in any polarity. The current flowing from the voltage source 45 into the change-over unit 51 is measurable via a precision measurement resistor 52 connected in series. The voltage drop at the resistor 52 is applied to a second PGA amplifier 43, whose output signal may be connected via a multiplexer 54 in turn to the same A/D converter 49 as the first PGA amplifier 41. The use of a common A/D converter for the voltage measuring device 41, 49 and the current measuring device 52, 43, 49 reduces the construction outlay and eliminates sources of error. There is connected before the PGA amplifiers 41, 43 in each case a sample and hold circuit 42, 44 with a clock input 42a or 44a.

The changeover unit 51 (FIG. 4) comprises with expediency a switching matrix 53, which has four columns 1 to 4 for the connection of the electric voltage source 45 and the voltage measuring device 41, 49. The number of rows corresponds to the number of contacts of the analysis element. Four rows A-D for the connection of the four unit contacts 21a to 21d are shown.

If the analysis element has a smaller or greater number of contacts, the switching matrix has with expediency an identical number of rows of switches. In FIG. 3 there are shown for example eight rows of switches A to H, so that up to eight unit contacts 21a-21h and hence element contacts of corresponding analysis elements may be connected optionally and in any polarity both with the voltage source 45 and with the voltage measuring device 41, 49 if the corresponding switching nodes 55 of the switching matrix 53 are closed.

The switching matrix may naturally have a larger number of columns, in order for example that further measurement devices may be connected to the analysis element. Conversely a changeover unit 51 as defined in the present invention does not necessarily have to be constructed as a complete switching matrix in the sense that each contact in each polarity may be connected both to the electric voltage source 45 and to the voltage measuring device 41, 49. It is sufficient if the changeover device comprises the switches required in order to make the respective desirable control functions possible. A complete switching matrix is preferred, however, since optimum checking of the sensor before and during the measurement may thereby take place.

The triggering of the switching nodes 55 of the switching matrix 53 takes place by means of the switching matrix control logic 39, which may be clocked via a clock input 39a and forms part of the changeover unit 51.

The function of the system shown in FIG. 3 is explained below in different operating states. The respective closed switching nodes of the switching matrix 53 are defined there by stating the corresponding number of the column or the letter of the row.

In the first operating state the analysis element 10 is not yet connected to the unit contacts 21. In said state the function of the unit is checked. In particular it is checked whether, for example through contaminants, a (partial) short-circuit has occurred between the unit contacts 21a to 21d. In order to conduct said check, for example for the contacts 21a and 21b, the switching nodes A1 and B2 (or B1 and A2) are closed. At a defined voltage of the voltage source 45 the current flow measured by the current measuring device 52, 43, 49 produces a measure for the resistance between the contacts, which is compared by the measuring and control unit 30, which in this case serves as a discriminator device, with a limit value which is stored in the calibration value store 37. If the measured resistance value is less than the limit value, a fault signal is displayed and the unit switched into a "malfunction" state in which measurement is impossible.

Said check may be carried out successively with all the contacts 21a to 21d.

In the next operating state the connection of the analysis element 10 is detected. To this end the switching nodes A1 and D2 (or D1 and A2) are closed. If the contact between the element contacts 17 and the unit contacts 21 is closed, a current flows, which is determined by means of the current measuring device 52, 43, 49. Said mode of operation is made possible by the second connecting lead 16d, which is connected to at least one electrode (here the working electrode 13). The detection of the analysis element may be realized conventionally, for example by means of a microswitch. According to the invention it is possible with reduced outlay.

After the connection of the analysis element 10 there is determined in the same operating state the resistance between the contacts 17a and 17d in a similar fashion as for the first operating state. In this case a comparison takes place with a limit value which corresponds to the resistance of intact connecting leads 16a, 16d to the working electrode 13. If there are hairline cracks in said connecting leads, the resistance is increased. If the measured resistance lies above the defined limit value, a fault indication that the analysis element 10 is defective takes place.

In a third operating state a short-circuit test of the analysis element takes place. In order for example to test whether the required electrical insulation between the working electrode 13 and the auxiliary electrode 15 is present, the switching nodes C1 and D2 (or D1 and C2) are closed. There takes place once again a resistance measurement and comparison with a limit value, a fault signal being generated if the limit value is not reached.

A fourth operating state serves to determine the wetting of the electrodes 13, 14 and 15 with the sample and—in a preferred embodiment—to check the completeness of the wetting.

For the determination of the wetting the switching nodes are closed in such a way that a resistance measurement takes place between two of the electrodes. These may be for example the reference electrode 14 and the auxiliary electrode 15, the switching nodes B1 and C2 (or C1 and B2) being closed. The wetting of the electrodes leads to a drop in the resistance, which may be determined as in the preceding operating states. In said position of the switching matrix 53 there may be checked at the same time the resistance of the connecting leads 16b and 16c leading to the reference electrode 14 and to the auxiliary electrode 15 and hence the correct state of said connecting leads.

The accuracy of the analysis is in the case of an amperometric determination dependent on the fact that the active surface of the working electrode 13 is completely wetted. A check is possible according to a preferred embodiment by means of a capacitance measurement (i.e. the measurement of a complex resistance). For this the voltage source 45 is connected between the working electrode 13 and the reference electrode 14 by closure of the switching nodes A1 and B2 (or B1 and A2). The voltage is measured with high impedance ("zero current") between the auxiliary electrode 15 and the working electrode 13, for which purpose the switching nodes C3 and D4 (or C4 and D3) are closed.

The measurement of the capacitance requires a time resolved current-voltage measurement. For this the voltage source 45 may be formed as an a.c. voltage source, whose frequency is preferably settable. Particularly preferably, however, the measurement of a complex resistance takes place by comparatively rapid electronic components being used and the voltage and current signals being measurable or triggerable in synchrony (by triggering of the clock inputs 39a, 42a, 44a, 54a and 47a). In this way it is possible to monitor in time the relaxation process during the switching on or off of the voltage source 45 and hence to determine the capacitance between the working electrode and the auxiliary electrode, which is a measure for the wetting of the working electrode.

In this connection it is once again helpful if the working electrode 13 comprises two connecting leads 16a, 16d to the measuring and evaluation circuit 23. In this way it is possible to measure the voltage between the auxiliary electrode 15 and the working electrode 13 with zero current, and hence uninfluenced by the lead resistances, by means of the lead 16d, while the lead 16a serves for the current feed.

For the wetting check the functions of the auxiliary electrode 15 and the reference electrode 14 and of the two connecting leads 16a and 16d may naturally be interchanged. It is preferable that the resistance or capacitance measurement be carried out twice, and that during the second measurement the voltage source 45 be connected between the working electrode 13 and the auxiliary electrode 15 and the voltage be measured with zero current between the reference electrode 14 and the working electrode 13.

In a fifth operating state the electrochemical measurement takes place. The voltage source is here connected between the auxiliary electrode and the working electrode by closure of the switching nodes C1 and D2 (or C2 and D1). The voltage is measured between the reference electrode and the working electrode, to which end the switching nodes A3 and B4 (or A4 and B3) are closed. As is usual during the measurement of amperometric sensors with three electrodes, the output voltage of the voltage source 45 is regulated so that the voltage between the reference electrode 14 and the working electrode 13 has a desired target value. The current thereby flowing between the auxiliary electrode and the working electrode is a measure for the analysis. In this context also the additional connecting lead at the working electrode is helpful. If it were not present, the same contact of the working electrode would have to be used both for the current feed and for the voltage measurement. The voltage measurement would be distorted by the voltage drop at the resistance of the connecting lead 16a. Due to the additional connecting lead 16d it is possible to measure the voltage with zero current. The resistance of the connecting leads 16a to 16d therefore has no influence on the measurement result.

As mentioned, the working electrode 14 and the auxiliary electrode 15 are preferably of identical construction. In this way a further optional control function is possible, with which the voltage between the reference electrode and the auxiliary electrode is measured by closure of the switching nodes B3 and C4 (or B4 and C3) after wetting with the sample. The measured voltage must be practically equal to zero if the electrodes are in a correct electrochemical state.

The preceding control functions describe some important examples and some important variants, in which the changeover unit 51 may be used. The skilled man is however conversant on the basis of the preceding description with numerous alternatives, with which the same and in some cases additional control, checking and measurement functions may be realized with a low outlay on technical equipment.

Figure 6:
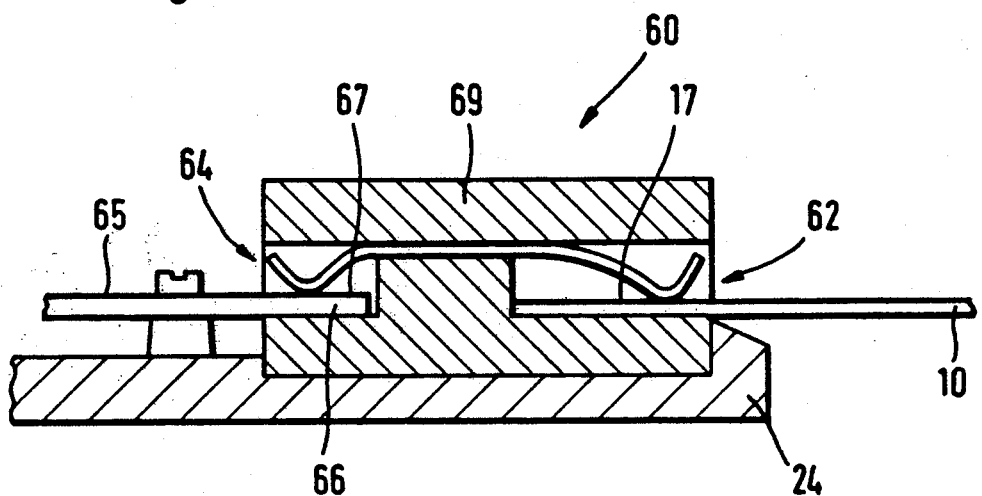
FIGS. 5 and 6 show a direct plug connector of an analysis system in top view and in section.
Figure 5:
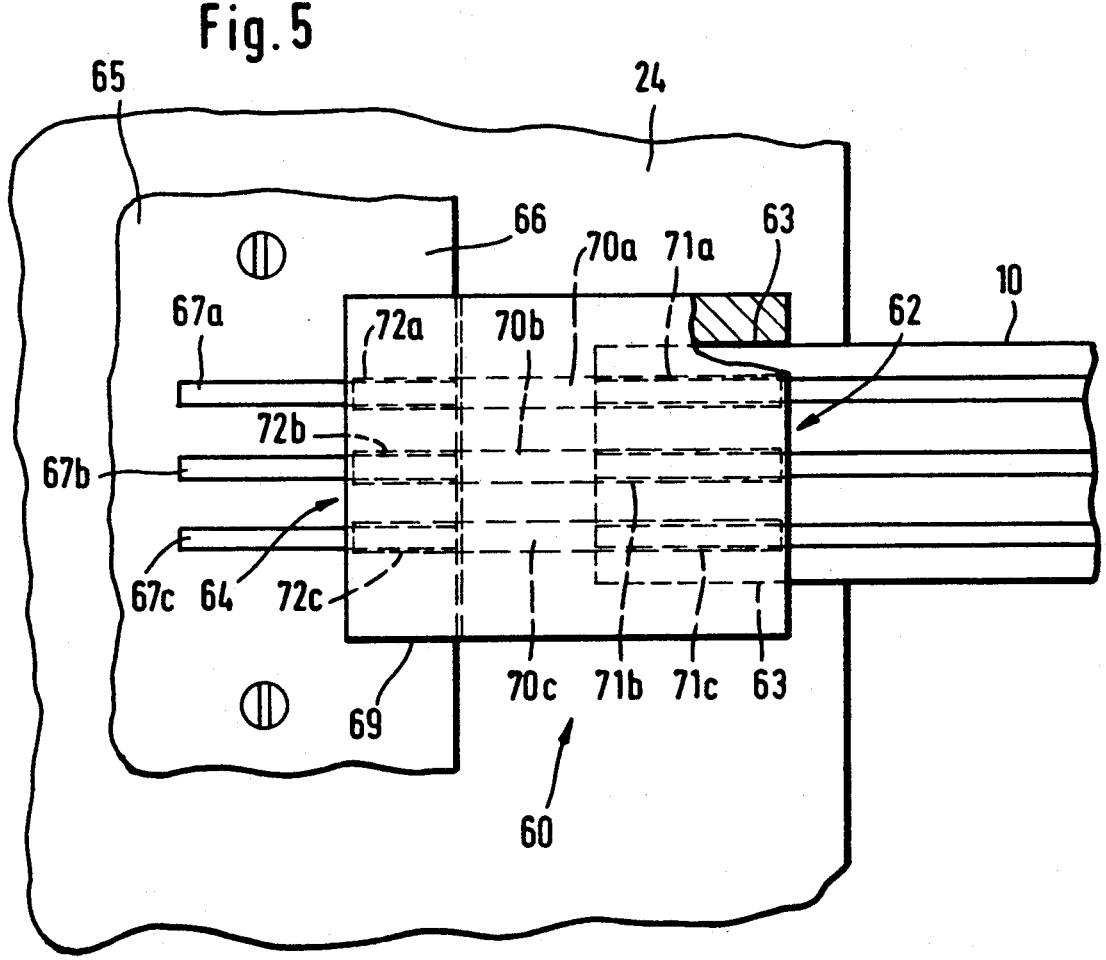

FIGS. 5 and 6 show a design of the analysis element connection 22, said design being used particularly preferably in conjunction with the analysis system described above, but also having importance on its own.

A direct plug connector 60 comprises two plugging zones 62, 64, the first plugging zone 62 serving for the connection of the analysis element 10 and the second plugging zone 64 for the connection of the measuring and evaluation circuit. A printed circuit board 65, which carries the measuring and evaluation circuit (not shown in the figure), comprises a plug strip 66 with plugs 67, which penetrates into the second plugging zone 64.

The plugging zones 62, 64 are formed by recesses in a preferably one-piece housing 69. They are connected to one another by one-piece contact spring parts 70a, which comprise respectively outside contact springs 71a–71c for the contacting of the connection contacts 17a–17c of the analysis element and inside contact springs 72a–72c for the contacting of the plugs 67 of the printed circuit board 66.

The direct plug connector 60 is connected in a mechanically stable manner to the housing 24 of the evaluation unit 20. The analysis element 10 is guided laterally by the side walls 63 of the first plugging zone 62 during the plugging-in.

Said construction makes a mechanical tolerance balancing (thermal expansion tolerance and dimensional tolerance) between printed circuit board 65 and housing 24 possible, without the contacting being jeopardized. In this way mechanical loading is avoided. The construction is extremely simple and inexpensive to manufacture. It is to this extent superior to previously known problem solutions, in which an additional adaptor plug or soldered connections have been used.

What is claimed is:

1. An electrochemical analysis system for the analytical determination of a constituent of a sample, said system comprising:

a disposable analysis element which includes an isolating carrier with a sample application means for applying a sample thereto for analysis, at least one sensor means with a working electrode and a reference electrode for sensing electrical properties of the sample on the sample application means, and a connection zone with element connecting contacts which are connected to the electrodes via connecting leads; and an evaluation unit which includes an analysis element connector means with unit contacts for electrically connecting to the element connecting contacts of said analysis element, and a measuring and evaluation circuit means for measuring electrical variation characteristics of the electrical properties sensed by the at least one sensor means on said analysis element and for converting a measured value into an analytical value, the measuring and evaluation circuit means including an electrical power source with a current measuring device, a voltage measuring device, and a changeover unit connected on one side to the electrical power source with said current measuring device and said voltage measuring device and another side of said changeover unit connected to said connector means with said unit contacts, said changeover unit comprising switching means for selectively connecting said electrical power source with said current measuring device and said voltage measuring device to different pairs of unit contacts in said connector means.

2. An electrochemical analysis system according to claim 1, wherein the changeover unit incorporates a switching matrix.

3. An electrochemical analysis system according to claim 1, wherein the changeover unit, the voltage measuring device and the power source are integrated together monolithically.

4. An electrochemical analysis system according to claim 1, wherein said evaluation unit further includes discriminator means for determining an electrical resistance based on a voltage of the power source and a measured signal of the current measuring device, and for generating a fault signal based on whether the determined electrical resistance is at least one of below and above a predetermined resistance limit value.

5. An electrochemical analysis system according to claim 1, wherein the measuring and evaluation circuit further includes a microprocessor-controlled digital signal processing unit operatively connected to the current measuring device and the voltage measuring device so as to digitally control the electrical power source and the changeover unit.

6. An electrochemical analysis system according to claim 1, wherein each of the voltage measuring device and the current measuring device include means for determining complex signal components.

7. An electrochemical analysis system according to claim 1, wherein said evaluation unit further includes clocking means operatively connected to the changeover unit, the voltage measuring device and the current measuring device, for clocking the changeover unit, the voltage measuring device and the current measuring device in synchrony.

8. An electrochemical analysis system according to claim 1, wherein said evaluation unit further includes a sample and hold circuit operatively connected between the changeover unit and the voltage measuring device.

9. An electrochemical analysis system according to claim 1, wherein said evaluation unit further includes a sample and hold circuit operatively connected between the changeover unit and the measuring device.

10. An electrochemical analysis system for the analytical determination of a constituent of a sample, said system comprising:

a disposable analysis element which includes an isolating carrier with a sample application means for applying a sample thereto for analysis, at least one sensor means with a working electrode and a reference electrode for sensing electrical properties of the sample on the sample application means, and a connection zone with connecting contacts which are connected to the electrodes via connecting leads, wherein at least one of the electrodes is connected to at least two of said connecting contacts via at least two connecting leads; and an evaluation unit which includes an analysis element connector means for electrically connecting to the connecting contacts of said analysis element, and a measuring and evaluation circuit means for measuring electrical variation characteristics of the electrical properties sensed by the at least one sensor means on said analysis element and for converting a measured value into an analytical value, the measuring and evaluation circuit means including a changeover means for changing over connection of at least one of an electrical power source with a current measuring device and a voltage measuring device to different connecting contacts of the analysis element.

11. An electrochemical analysis system according to claim 10, wherein the electrode to which the additional connecting lead is connected is the working electrode.

12. An electrochemical analysis system according to any one of claim 10, wherein the at least one sensor includes an additional auxiliary electrode.

13. An electrochemical analysis system according to claim 12, wherein a composition of the auxiliary electrode and a composition of the reference electrode are the same.

14. An electrochemical analysis system according to claim 11, wherein the working electrode is arranged between the reference electrode and the auxiliary electrode.

15. An electrochemical analysis system for the analytical determination of a constituent of a sample, comprising:

disposable analysis elements, which comprise on an isolating carrier in a sample application zone at least one sensor with a working electrode and a reference electrode and in a connection zone connecting contacts, wherein the electrodes and the connecting contacts are connected via connecting leads and the electrical properties of the analysis elements measurable from the connecting contacts vary on contact with the sample in a manner characteristic of the analysis, and an evaluation unit, which comprises an analysis element connection with unit contacts for the electrical connection to the connecting contacts of the analysis elements, and a measuring and evaluation circuit for measuring the electrical variation characteristic of the analysis and conversion of the measured value into an analytical value, wherein the analysis element connection comprises a direct plug connector with two plugging zones, wherein the first plugging zone serves for the connection of the analysis element and the second plugging zone for the connection to plugs of a printed circuit board, which contains at least a part of the measuring and evaluation circuit, the plugging zones are connected to one another by contact spring parts, which comprise respectively outside contact springs in the first plugging zone for the contacting of the connecting contacts of the analysis element and inside contact springs for the contacting of the plugs of the printed circuit board.

* * * * *